United States Patent
Bellhouse et al.

[11] Patent Number: 6,013,050
[45] Date of Patent: Jan. 11, 2000

[54] PARTICLE DELIVERY

[75] Inventors: Brian John Bellhouse; Paul Rudd Drayson; John Christopher Greenford; David Francis Sarphie, all of Oxfordshire, United Kingdom

[73] Assignee: PowderJect Research Limited, United Kingdom

[21] Appl. No.: 08/847,430

[22] Filed: Apr. 24, 1997

Related U.S. Application Data

[63] Continuation-in-part of application No. PCT/GB95/02498, Oct. 20, 1995.

[51] Int. Cl.[7] ...................................................... A61M 5/30
[52] U.S. Cl. ................................................. 604/70; 604/68
[58] Field of Search ................................. 604/68–72, 88, 604/139, 140, 141, 240, 243

[56] References Cited

U.S. PATENT DOCUMENTS

| | | |
|---|---|---|
| 3,788,315 | 1/1974 | Laurens . |
| 3,906,950 | 9/1975 | Cocozza . |
| 3,949,751 | 4/1976 | Birch et al. . |
| 4,596,556 | 6/1986 | Morrow et al. . |
| 4,945,050 | 7/1990 | Sanford et al. . |
| 5,049,125 | 9/1991 | Accaries et al. ........................... 604/70 |
| 5,062,830 | 11/1991 | Dunlap . |
| 5,149,655 | 9/1992 | McCabe et al. . |
| 5,157,207 | 10/1992 | Carlson et al. ...................... 424/93.4 X |
| 5,204,253 | 4/1993 | Sanford et al. . |
| 5,371,015 | 12/1994 | Sanford et al. . |
| 5,503,627 | 4/1996 | McKinnon et al. ................... 604/68 X |
| 5,630,796 | 5/1997 | Bellhouse et al. . |

FOREIGN PATENT DOCUMENTS

| | | |
|---|---|---|
| 0 406 778 A1 | 1/1991 | European Pat. Off. . |
| 2 360 031 | 8/1978 | France . |
| WO 92/04439 | 3/1992 | WIPO . |
| WO 94/24263 | 10/1994 | WIPO . |
| WO 95/19799 | 7/1995 | WIPO . |
| WO 96/12513 | 5/1996 | WIPO . |

*Primary Examiner*—Wynn Wood Coggins
*Assistant Examiner*—A. T. Nguyen
*Attorney, Agent, or Firm*—Thomas P. McCracken

[57] ABSTRACT

A needleless syringe particle delivery system is provided. The needleless syringe comprises an elongate nozzle which is connected at its upstream end to an open ended capsule chamber. The capsule chamber is configured to house and intimately enclose a nonrigid capsule containing particles of a therapeutic agent. An opening means is provided at the upstream end of the capsule chamber, and is used to pierce the upstream end of a capsule in the chamber. After the capsule is opened, an energizing means connected to the upstream end of the capsule chamber applies a gaseous pressure sufficient to force the particles out of the capsule and the open downstream end of the capsule chamber and thus to create through the nozzle a supersonic gas flow in which the particles are entrained.

16 Claims, 1 Drawing Sheet

PARTICLE DELIVERY

CROSS-REFERENCE TO RELATED APPLICATION

This application is a continuation-in-part of International Patent Application Number PCT/GB95/02498, filed Oct. 20, 1995, designating the United States, from which priority is claimed pursuant to 35 U.S.C. §365(c) and which is incorporated herein by reference in its entirety.

TECHNICAL FIELD

The present invention relates generally to a needleless syringe for use in delivery of particles of a therapeutic agent to a target surface. More particularly, the invention is drawn to a needleless syringe system that is configured for delivery of particles of a therapeutic agent from a nonrigid capsule containing such particles by way of a supersonic gas flow.

BACKGROUND OF THE INVENTION

In copending, commonly owned U.S. application Ser. No. 08/474,367, now U.S. Pat. No. 5,630,796, a noninvasive delivery system is described that entails the use of a needleless syringe. The syringe is used for transdermal delivery of powdered therapeutic compounds and compositions to skin, muscle, blood or lymph. The syringe can also be used in conjunction with surgery to deliver therapeutics to organ surfaces, solid tumors and/or to surgical cavities (e.g., tumor beds or cavities after tumor resection).

The needleless syringe is constructed as an elongate tubular nozzle, having a rupturable membrane initially closing the passage through the nozzle adjacent to the upstream end of the nozzle. Particles of a powdered therapeutic agent are located adjacent to the membrane. The therapeutic agent is delivered using an energizing means which applies a gaseous pressure to the upstream side of the membrane that is sufficient to burst the membrane, thereby producing a supersonic gas flow through the nozzle in which the particles are entrained.

SUMMARY OF THE INVENTION

Recent studies have shown that, by the appropriate selection of the geometry and Mach number for the nozzle in the needleless syringe described in U.S. application Ser. No. 08/474,367, now U.S. Pat. No. 5,630,796, it is possible to provide a pseudo-steady state, supersonic, two-phase flow through the nozzle. Particles that are disposed within this multi-phasic flow travel with a velocity close to that of the propelling gas in which they are entrained. The selected geometry for the nozzle preferably has a convergent upstream portion, leading through a throat to a cylindrical or, preferably, divergent downstream portion.

Consequently, a large proportion of the particles containing the therapeutic agent reach the target under quasi-steady flow conditions and only a small proportion are delivered in transient flow and carried on the contact surface. This leads to considerable benefit both in control and in increased skin or other target penetration, and is surprising in such a transient phenomenon.

In the syringe of U.S. application Ser. No. 08/474,367, particles of a powdered therapeutic agent to be delivered are contained within a replaceable capsule comprised of a pair of the rupturable membranes. The rupturable membranes are arranged in the syringe such that their surfaces (faces) are substantially transverse to the axis of the nozzle and thus provide an upstream and a downstream membrane. The membranes are further sealed together around their edges to provide a container for the powdered agent by means of an intervening ring. The intervening ring also provides sealing means for sealing the periphery of the assembled capsule to a tubular body of the syringe. A capsule of this construction is quite complex for a disposable part, and may provide an uncertain dose of the therapeutic agent if a proportion of the particles become entrapped behind the edges of the downstream membrane upon its rupture during delivery.

In accordance with the present invention, then, a needleless syringe is constructed as an elongate nozzle, at the upstream end of which is an open capsule chamber in axial alignment with the nozzle. The open capsule chamber is configured to contain and intimately enclose a soft-walled capsule containing particles of a therapeutic agent for delivery from the syringe. A means is provided at the upstream end of the capsule chamber for piercing the upstream end of a capsule when housed within the chamber. After the capsule has been pierced, an energizing means is used to apply through the open upstream end of the capsule chamber a gaseous pressure providing a gas flow sufficient to force the particles out through the downstream end of the capsule and into the nozzle. This, in turn, allows particles of the therapeutic agent, entrained within the gas flow provided by the energizing means, to pass through the nozzle with a velocity approaching supersonic speeds of the driving gas flow.

The capsule for use in the present invention can incorporate a gelatin wall and have a substantially cylindrical configuration with domed ends. Such capsule configurations are known in the art, and are used, for example, in bronchial or respiratory drug inhaler devices. Technology for creating and filling such capsules is therefore readily available and well known in the art.

A number of alternative configurations can be used in the construction of the present syringe device. For example, the capsule chamber which encloses and positions the capsule within the syringe may be provided by the combination of two separable wall portions which are divided in a direction transverse to the major axis of the elongate nozzle. In use, the two chamber wall portions can be separated to allow insertion of a capsule, and then closed to encase the capsule. The two wall portions of the chamber may be held together in a number of ways, for example, by entrapment between two parts of the syringe body which are interconnected by a coupling such as a threaded, bayonet, or other releasable connection.

Once in place within the syringe, the capsule is opened on its upstream end to accommodate delivery of the therapeutic agent from the capsule. Means for opening the upstream end of the capsule can employ a piercing or lancing device, such as a tubular cutter or a like sharp projection, that depends from the upstream end of the capsule wall and protrudes into the capsule chamber. Such an opening means can be used to breach the upstream end of the capsule as the two portions of the chamber wall are brought together around the capsule. Alternatively, the upstream end of the capsule may be pierced open by a needlelike member which is extended into the capsule chamber through its upstream opening after the chamber walls are closed around the capsule.

The downstream end of the capsule may be opened similarly to the upstream end in order to ensure that, upon delivery, the therapeutic agent will readily pass through the downstream ends of the capsule and capsule chamber, and pass into the nozzle. Alternatively, the downstream end of the capsule may be molded or otherwise formed with a weakened portion, such as in a cruciform shape, so that the downstream end of the capsule readily ruptures when the necessary gas pressure is applied to initiate the gas flow through the capsule and along the nozzle.

In some cases, it may be desirable to provide an increased gas pressure build-up in the device prior to launch of the supersonic gas flow, thereby increasing the supersonic velocity attainable during delivery. For example, the interface between the capsule chamber and the nozzle may be closed initially by a rupturable membrane, for example a Mylar membrane. The rupturable membrane can thus provide a wide variety of burst points, allowing for a range of pressure build up prior to delivery. In addition, a fine mesh or other retaining means can be positioned at or near the rupturable membrane in order to retain any parts of the capsule wall which might otherwise be entrained in the gas flow through the nozzle.

A number of suitable energizing means can be used with the present needleless syringe devices. For example, a chamber containing a reservoir of compressed gas can be arranged upstream of the capsule chamber. The gas can be released from the energizing chamber by way of a pierceable membrane or a valve, such as a spring-loaded ball valve, which is actuated by either mechanical means or by manual manipulation, for example, by movement of two parts of the syringe relative to each other. Alternatively, the energizing chamber can be fitted with means for providing a controlled build-up of gaseous pressure from an upstream or associated source.

Reference is made to U.S. application Ser. No. 08/474,367 now U.S. Pat. No. 5,630,796, for other aspects of the needleless syringe, for example, the use of a spacer/silencer at the downstream end of the nozzle, various alternative nozzle geometries, types of therapeutic agent particles which may be delivered, and the composition, and pressure, of the driving gas to be used.

BRIEF DESCRIPTION OF THE FIGURES

An example of a syringe constructed in accordance with the present invention is illustrated in the accompanying drawings, in which.

DETAILED DESCRIPTION OF THE PREFERRED EMBODIMENTS

Figure 1:
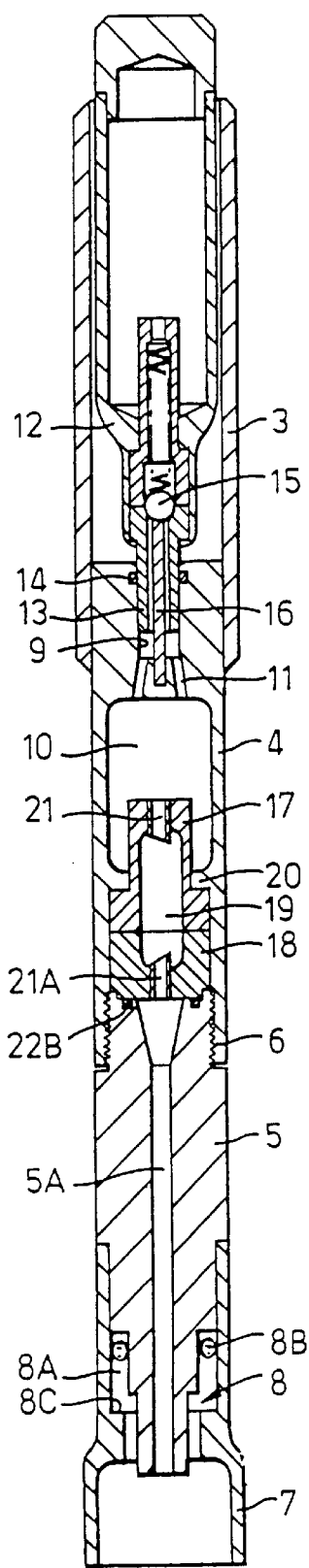
FIG. 1 is an axial section through one embodiment of the invention.

Before describing the present invention in detail, it is to be understood that this invention is not limited to particular pharmaceutical formulations or process parameters as such may, of course, vary. It is also to be understood that the terminology used herein is for the purpose of describing particular embodiments of the invention only, and is not intended to be limiting.

All publications, patents and patent applications cited herein, whether supra or infra, are hereby incorporated by reference in their entirety.

It must be noted that, as used in this specification and the appended claims, the singular forms "a", "an" and "the" include plural referents unless the content clearly dictates otherwise. Thus, for example, reference to "a therapeutic agent" includes a mixture of two or more such agents, reference to "a gas" includes mixtures of two or more gases, and the like.

A. Definitions

Unless defined otherwise, all technical and scientific terms used herein have the same meaning as commonly understood by one of ordinary skill in the art to which the invention pertains. The following terms are intended to be defined as indicated below.

The term "transdermal" delivery captures both transdermal (or "percutaneous") and transmucosal administration, i.e., delivery by passage of a therapeutic agent through the skin or mucosal tissue. See, e.g., *Transdermal Drug Delivery: Developmental Issues and Research Initiatives,* Hadgraft and Guy (eds.), Marcel Dekker, Inc., (1989); *Controlled Drug Delivery: Fundamentals and Applications,* Robinson and Lee (eds.), Marcel Dekker Inc., (1987); and *Transdermal Delivery of Drugs,* Vols. 1–3, Kydonieus and Berner (eds.), CRC Press, (1987). Aspects of the invention which are described herein in the context of "transdermal" delivery, unless otherwise specified, are meant to apply to both transdermal and transmucosal delivery. That is, the compositions, systems, and methods of the invention, unless explicitly stated otherwise, should be presumed to be equally applicable to transdermal and transmucosal modes of delivery.

As used herein, the terms "therapeutic agent" and/or "particles of a therapeutic agent" intend any compound or composition of matter which, when administered to an organism (human or nonhuman animal) induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. More particularly, the term "therapeutic agent" includes compounds or compositions for use in all of the major therapeutic areas including, but not limited to, anti-infectives such as antibiotics and antiviral agents; analgesics and analgesic combinations; local and general anesthetics; anorexics; antiarthritics; antiasthmatic agents; anticonvulsants; antidepressants; antihistamines; anti-inflammatory agents; antinauseants; antineoplastics; antipruritics; antipsychotics; antipyretics; antispasmodics; cardiovascular preparations (including calcium channel blockers, beta-blockers, beta-agonists and antiarrythmics); antihypertensives; diuretics; vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like).

Particles of a therapeutic agent, alone or in combination with other drugs or agents, are typically prepared as pharmaceutical compositions which can contain one or more added materials such as carriers, vehicles, and/or excipients. "Carriers," "vehicles" and "excipients" generally refer to substantially inert materials which are nontoxic and do not interact with other components of the composition in a deleterious manner. These materials can be used to increase the amount of solids in particulate pharmaceutical compositions. Examples of suitable carriers include water, silicone, gelatin, waxes, and like materials. Examples of normally employed "excipients," include pharmaceutical grades of dextrose, sucrose, lactose, trehalose, mannitol, sorbitol, inositol, dextran, starch, cellulose, sodium or calcium phosphates, calcium sulfate, citric acid, tartaric acid, glycine, high molecular weight polyethylene glycols (PEG), and combinations thereof. In addition, it may be desirable to include a charged lipid and/or detergent in the pharmaceutical compositions. Such materials can be used as stabilizers, anti-oxidants, or used to reduce the possibility of local irritation at the site of administration. Suitable charged lipids include, without limitation, phosphatidylcholines (lecithin), and the like. Detergents will typically be a nonionic, anionic, cationic or amphoteric surfactant. Examples of suitable surfactants include, for example, Tergitol® and Triton® surfactants (Union Carbide Chemicals and Plastics, Danbury, Conn.), polyoxyethylenesorbitans, e.g., TWEEN® surfactants (Atlas Chemical Industries, Wilmington, Del.), polyoxyethylene ethers, e.g., Brij, pharmaceutically acceptable fatty acid esters, e.g., lauryl sulfate and salts thereof (SDS), and like materials.

"Gene delivery" refers to methods or systems for reliably inserting foreign nucleotide sequences, either DNA or RNA, into a recipient's cells. Such methods can result in expression of non-integrated transferred nucleotide sequences, extrachromosomal replication and expression of transferred replicons (e.g., episomes), or integration of transferred genetic material into the genomic DNA of the recipient's cells.

By "vector" is meant any genetic element, such as a plasmid, phage, transposon, cosmid, chromosome, virus, virion, etc., which is capable of replication when associated with the proper control elements and which can transfer gene sequences between cells.

B. General Methods

Figure 2:
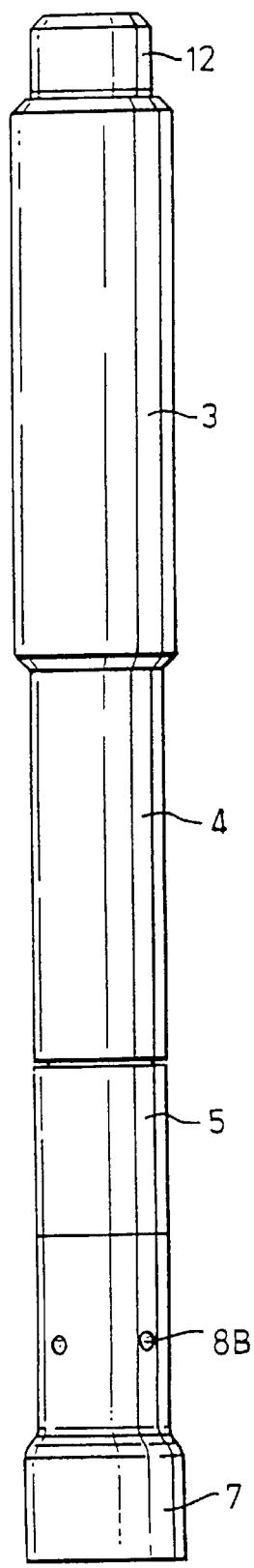
FIG. 2 is a side elevation of the embodiment of FIG. 1.

One embodiment of the needleless syringe of the present invention is shown in FIGS. 1 and 2. The syringe has a barrel portion formed by rigidly interconnected upper and lower barrel parts, respectively indicated at 3 and 4, and a tubular nozzle 5, which has a convergent/divergent passage 5A. The nozzle 5 is connected, at the upstream end thereof, to the lower barrel part 4 by way of screw-threads 6. The downstream end of the nozzle 5 is provided with a shroud 7 and a silencer, generally indicated at 8. The lower barrel part 4 has a passageway 9 that interconnects the interior of the upper barrel part 3 with a compartment 10 via a ring of ducts 11. The upper barrel part 3 is arranged to receive through its open upper end a container 12 housing pressurized gas and having a neck 13 which is insertable downwards into the passage 9, to which it is sealed by an O-ring 14. The outlet from the gas container 12, which passes through the neck 13 of the container, is closed by a spring-loaded ball valve 15. A spigot 16 which is fixed in the lower barrel part 4 and extends into the neck 13 of the gas container, is actuate the ball valve to an open position against the spring bias when the gas container is urged from its initial position as depicted in the Figure, and travels further down into the upper barrel part 3, for example by pressure exerted by the thumb of a person's hand when holding the barrel in its palm.

Figure 3:
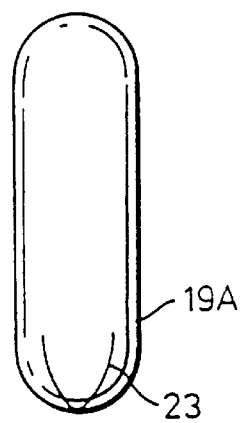
FIG. 3 is a side elevation view of a capsule for use in the invention.

A capsule chamber 19 is arranged between the lower barrel part 4 and the nozzle 5, and interfaces at its downstream end with the upstream end of the nozzle. In the embodiment depicted in FIG. 1, the capsule chamber is formed by two hollow syringe parts 17 and 18. When brought together as illustrated, these parts define an internal housing of substantially cylindrical shape with domed ends, wherein the housing is configured to contain a nonrigid capsule of complementary shape, such as the capsule 19A depicted in FIG. 3. The capsule contains particles of a therapeutic agent which are to be delivered from the needleless syringe. The hollow syringe parts 17 and 18 are held together between the nozzle 5 and an inwardly projecting rib 20 on the lower barrel part 4 when the barrel is connected to the nozzle. In this regard, attachment of the barrel portion to the nozzle resiliently holds the syringe parts 17 and 18 together to provide the capsule chamber 19. The upper and lower ends of the syringe parts 17 and 18 are both provided with fixed tubular opening means 21, 21A which are arranged to pierce the ends of the capsule when the parts 17 and 18 are drawn together by the attachment of the lower barrel part 4 to the nozzle 5 when the capsule is in place within the capsule chamber.

In this assembled configuration, the downward travel of the gas canister relative to the upper barrel part 3 causes the spigot 16 to actuate the ball valve 15 to an open position, thereby releasing gas pressure which then flows through ring of ducts 11 into compartment 10, and then into the upper end of the capsule chamber 19. When sufficient pressure has built up, a supersonic flow is created through the interior passage in the nozzle 5, with the particles of the therapeutic agent being flushed out of the capsule and entrained in the gas flow, and hence carried out through the shroud into a target surface.

Figure 4:
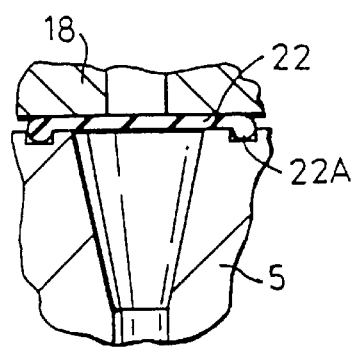
FIG. 4 is an enlarged view a part of a modified syringe constructed according to the invention.

Referring now to FIG. 4, a rupturable membrane 22, for example a membrane comprised of a suitable polymeric material such as MYLAR® and which is rupturable by release of a gas flow from the energizer means may be arranged near the interface between the downstream end of the capsule chamber and the upstream end of the nozzle 5, for example, trapped between the bottom of the chamber part 18 and the upper end of the nozzle 5. Similarly, a screen can be used in place of the rupturable membrane, or in conjunction with the rupturable membrane, in order to retain any portions of a ruptured capsule wall which might otherwise travel into the nozzle during delivery of the therapeutic agent. The membrane 22 can be provided at its edges with a lip 22A, which is received in an annular grove in the top face of the nozzle 5, thereby providing a sealed connection between the nozzle 5 and the syringe part 18. The lip 22A thus replaces the O-ring 22B shown in FIG. 1.

After discharge of the syringe, the barrel part 4 can be disconnected from the nozzle 5 to enable removal and disposal of the remnants of a spent capsule, and also of the rupturable membrane if used. The gas canister 12 can also be withdrawn for disposal. In most cases the remaining parts of the syringe can then be reused once fitted with new disposable parts, e.g., a new capsule and gas canister.

In alternative embodiments, the lower opening means 21 can be removed, and a capsule having a weakened portion at a lower end thereof can be provided. The capsule may be weakened, for example, by cruciform lines of weakness 23, as shown in FIG. 3.

Referring again to FIGS. 1 and 2, the shroud and silencer 7 and 8, are similar to those described in copending U.S. application Ser. No. 08/474,367 to the extent that the shroud is a tubular part extending beyond the end of the nozzle 5, and the silencer includes an annular passage 8A between an upper portion of the shroud 7 and a lower portion of the nozzle S. Furthermore, a passage is also provided which leads from within the shroud 7 to a ring of vents 8B opening out through the upper part of the shroud to the atmosphere. The interior of the passageway is irregular in the sense that both the inner wall of the shroud and the outer wall of the nozzle are stepped as shown at 8C, thereby providing surfaces for the flow resulting from reflection of the shockwave at the target surface, to make multiple subsequent reflections, and thus dissipating the energy and noise. There may be a plurality of the steps 8C at axially spaced positions along the shroud and nozzle, with at least some adjacent pairs facing each other diagonally across the passage 8A, in a similar way to that in which the steps 8C face one another.

Alternatively, instead of being provided with the steps 8C, the passage may be filled with a helical vane, which causes multiple reflections from adjacent axially facing turns of the vane as the gas flow passes generally helically along the passage. Such a helical vane may be formed by molding a helical flight on the outside of the nozzle and a complementary helical flight on the inside of the shroud, the two being brought into angular alignment when the shroud is fitted to the nozzle.

These constructions of silencer form independent features of the invention and may be used with any needleless syringe of the kind in which particles are entrained in a supersonic gas flow through a nozzle to the downstream end of which a shroud and silencer is fitted.

Typically, in each of the illustrated examples, the gas provided by the energizing means may be helium at a pressure of the order of 40 to 80 bar. However, any other suitable delivery gas may be used. The nozzle 5 may be of convergent/divergent, or convergent/cylindrical form with a length of between 50 and 100 mm, preferably 60 mm, and a throat diameter of between 1 and 10 mm, preferably between 1.5 and 5 mm.

The needleless syringes of the present invention can be used for transdermal delivery of powdered therapeutic compounds and compositions, for delivery of genetic material into living cells (e.g., gene therapy or nucleic acid vaccination), both in vivo and ex vivo, and for the delivery of biopharmaceuticals to skin, muscle, blood or lymph. The syringes can also be used in conjunction with surgery to deliver therapeutic agents, drugs, immunogens, and/or biologics to organ surfaces, solid tumors and/or to surgical cavities (e.g., tumor beds or cavities after tumor resection). In theory, practically any agent that can be prepared in a substantially solid, particulate form can be safely and easily delivered using the present devices.

Delivery of therapeutic agents from the above-described needleless syringe systems is practiced with particles having an approximate size generally ranging from 0.1 to 250 μm. For drug delivery, the optimal particle size is usually at least about 10 to 15 μm (the size of a typical cell). For gene delivery, the optimal particle size is generally substantially smaller than 10 μm. Particles larger than about 250 μm can also be delivered from the devices, with the upper limitation being the point at which the size of the particles would cause untoward damage to the skin cells. The actual distance which the delivered particles will penetrate a target surface depends upon particle size (e.g., the nominal particle diameter assuming a roughly spherical particle geometry), particle density, the initial velocity at which the particle impacts the surface, and the density and kinematic viscosity of the targeted skin or mucosal tissue. In this regard, optimal particle densities for use in needleless injection generally range between about 0.1 and 25 $g/cm^3$, preferably between about 0.9 and 1.5 $g/cm^3$, and injection velocities generally range between about 200 and 3,000 m/sec. With appropriate gas pressure, particles of a therapeutic agent having an average diameter of 10–70 μm are accelerated through the nozzle at velocities approaching the supersonic speeds of the driving gas flow.

Accordingly, novel needleless syringe delivery systems and methods for using the same are disclosed. Although preferred embodiments of the subject invention have been described in some detail, it is understood that obvious variations can be made without departing from the spirit and the scope of the invention as defined by the appended claims.

We claim:

1. A needleless syringe for administering particles of a therapeutic agent, said syringe comprising:

(a) an elongate nozzle having an upstream end;

(b) a capsule chamber interfaced with the upstream end of the nozzle to provide a chamber/nozzle interface, said chamber having an open upstream end and an open downstream end and providing a housing for containing a nonrigid capsule;

(c) opening means for mechanically piercing a nonrigid capsule when the capsule is arranged in the capsule chamber housing, said opening means arranged at the upstream end of the capsule chamber; and (d) energizing means connected to the upstream end of the capsule chamber, wherein said energizing means comprises a source of pressurized gas and can be actuated to provide a gas flow through the capsule chamber and nozzle.

2. The syringe of claim 1 further comprising a nonrigid capsule arranged within the capsule chamber housing, wherein said capsule contains particles of a therapeutic agent.

3. The syringe of claim 2, wherein the capsule comprises substantially nonrigid gelatin walls and is cylindrical in shape.

4. The syringe of claim 1, wherein the capsule chamber is comprised of two portions which can be separated from each other to allow access to the capsule chamber housing.

5. The syringe of claim 4 further comprising a barrel portion that encases the capsule chamber and is attached to the upstream end of the elongate nozzle.

6. The syringe of claim 5, wherein attachment of the barrel portion to the nozzle resiliently holds the two portions of the capsule chamber together.

7. The syringe of claim 1, wherein the opening means comprises a cutting device which projects into the upstream end of the capsule chamber.

8. The syringe of claim 6, wherein the opening means comprises a cutting device which projects into the upstream end of the capsule chamber.

9. The syringe of claim 8, wherein attachment of the barrel portion to the needle brings the opening means into position to open a capsule when placed within the capsule chamber housing.

10. The syringe of claim 1 further comprising a second opening means arranged at the downstream end of the capsule chamber.

11. The syringe of claim 2, wherein the capsule comprises a weakened portion which allows a downstream end of said capsule to rupture upon application of gas pressure from the energizing means, thereby initiating a gas flow through the capsule and nozzle.

12. The syringe of claim 1, wherein the chamber/nozzle interface is closed by a rupturable membrane.

13. The syringe of claim 1, wherein the energizing means comprises a gas container housing pressurized gas.

14. The syringe of claim 13 further comprising release means which can be actuated to release a gas flow from the gas container to pass into the capsule chamber.

15. The syringe of claim 14, wherein the release means comprises a valve that can be actuated between open and closed positions.

16. The syringe of claim 15, wherein the valve is actuated by movement of two parts of the syringe relative to each other.

* * * * *